(12) United States Patent
Gaskins et al.

(10) Patent No.: US 8,337,780 B2
(45) Date of Patent: Dec. 25, 2012

(54) APPARATUS FOR DEMINERALIZING OSTEOINDUCTIVE BONE

(75) Inventors: Barton D. Gaskins, Chesapeake, VA (US); Louis Ford, Virginia Beach, VA (US); Debra Moore-Smith, Salisbury, NC (US); Robert K. O'Leary, Deltaville, VA (US); Anne Wilson, Virginia Beach, VA (US); Lloyd Wolfinbarger, Jr., Norfolk, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

(21) Appl. No.: 12/683,002

(22) Filed: Jan. 6, 2010

(65) Prior Publication Data

US 2011/0027871 A1    Feb. 3, 2011

Related U.S. Application Data

(63) Continuation of application No. 10/732,799, filed on Dec. 11, 2003, now abandoned, which is a continuation-in-part of application No. 10/180,989, filed on Jun. 26, 2002, now Pat. No. 6,830,763, which is a continuation-in-part of application No. 09/655,711, filed on Sep. 5, 2000, now Pat. No. 6,534,095.

(60) Provisional application No. 60/152,272, filed on Sep. 3, 1999.

(51) Int. Cl.
*B01D 35/00* (2006.01)

(52) U.S. Cl. .................. 422/534; 422/547; 422/556

(58) Field of Classification Search ............ 422/99–102, 422/129, 130, 131, 135, 500, 534, 536, 547, 422/556
See application file for complete search history.

(56) References Cited

U.S. PATENT DOCUMENTS

| | | | | |
|---|---|---|---|---|
| 3,801,280 A | * | 4/1974 | Shah et al. | 436/2 |
| 3,802,272 A | * | 4/1974 | Bischoff et al. | 73/866 |
| 4,184,916 A | * | 1/1980 | Tolbert et al. | 435/394 |
| 4,649,118 A | * | 3/1987 | Anderson | 435/297.3 |
| 5,578,455 A | * | 11/1996 | Tosa et al. | 435/7.32 |
| 6,320,025 B1 | * | 11/2001 | Slavazza et al. | 530/334 |

* cited by examiner

*Primary Examiner* — Jill Warden
*Assistant Examiner* — Dwayne K Handy
(74) *Attorney, Agent, or Firm* — Morgan, Lewis & Bockius LLP

(57) ABSTRACT

The invention is directed to an apparatus for producing demineralized osteoinductive bone. The apparatus demineralizes bone by subjecting bone, including, for example, ground bone, bone cubes, chips, strips, or essentially intact bone, to either a rapid high volume pulsatile acidification wave process or to a rapid continuous acid demineralization process. The pulsatile acidification wave process includes subjecting bone to two or more rapid pulse/drain cycles in which one or more demineralizing acids is rapidly pulsed into a vessel containing bone, and after a desired period of time, is rapidly drained from the vessel. The continuous acid demineralization process includes subjecting bone to a continuous exchange of demineralizing acid solution in which the demineralizing acid solution is recirculated from the container holding the bone through an ion exchange media. Calcium and phosphate are thereby removed from the bone to produce a regenerated acid, and the regenerated acid is returned to the container holding the bone. Both processes allow bone to be rapidly demineralized to a precise and specific desired residual calcium level without sacrificing osteoinductivity.

20 Claims, 2 Drawing Sheets

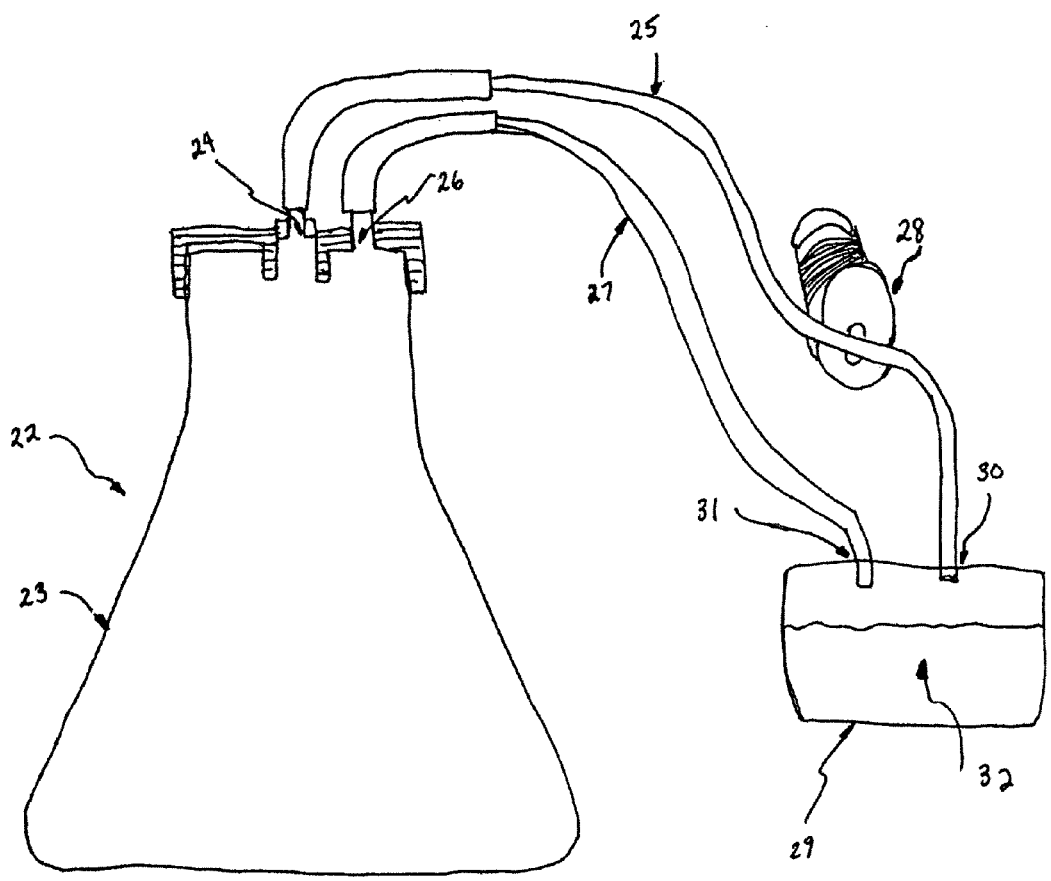

APPARATUS FOR DEMINERALIZING OSTEOINDUCTIVE BONE

CROSS-REFERENCE TO RELATED APPLICATIONS

This application is a continuation application of U.S. application Ser. No. 10/732,799, filed Dec. 11, 2003, which is a continuation-in-part of U.S. application Ser. No. 10/180,989, filed Jun. 26, 2002, (now U.S. Pat. No. 6,830,763; issued: Dec. 14, 2004), which is a continuation-in-part application of application Ser. No. 09/655,711, filed Sep. 5, 2002(now U.S. Pat. No. 6,534,095; issued Mar. 18, 2003), which claims the benefit of U.S. Provisional Application No. 60/152,272, filed Sep. 3, 1999, all which are herein incorporated by reference in their entireties.

FIELD OF THE INVENTION

The present invention relates to the preparation of bone grafts. The present invention further relates to the demineralization of osteoinductive bone.

BACKGROUND OF THE INVENTION

Demineralized freeze-dried bone allograft is widely used in the repair of skeletal defects and periodontal disease. It is known that the implantation of acid demineralized bone in the form of a powder in extraskeletal sites may stimulate new bone formation. Various groups including Syftestad, 1982; Urist et al., 1967; Urist and Strates, 1979; Urist and Strates, 1971; and Urist et al., 1983 have suggested that a noncollagenous protein or proteins present in demineralized bone has the ability to induce new bone formation when present within the implanted bone matrix.

Current procedures used to demineralize ground bone involve the use of ethanol to remove lipids and hydrochloric acid to remove the mineral components of bone. These known methods are problematic in that they require prohibitively long periods of time for processing resulting in a very low demineralization rate, require excessive handling of the ground bone being processed, are capable of processing only small amounts of ground bone, and result in a demineralized bone product which exhibits inferior osteoinductivity caused by excessive exposure of bone-inducing proteins in the bone to harsh acids over extended periods of time.

SUMMARY OF THE INVENTION

The present invention is directed to an apparatus for producing demineralized osteoinductive bone. The apparatus achieves demineralization of bone by subjecting bone to either a rapid high volume, pulsatile acidification wave process or to a rapid continuous exchange of acid.

In one embodiment of the invention, the apparatus for demineralizing osteoinductive bone comprises a container for holding demineralization solution and the osteoinductive bone; a vessel cap covering the container, the vessel cap containing a first port, and a second port for introducing the osteoinductive bone into the container; a filter tube assembly disposed within the first port for transporting the demineralization solution into and out of the container, the filter tube assembly being configured to exclude particles larger than a prescribed size; a pump for removing the demineralization solution from the container; and a first tube connecting the first port to the pump. The filter tube assembly preferably contains a plurality of openings along a predetermined portion thereof. Further, the filter tube assembly preferably is configured to exclude particles larger than 300μ, more preferably is configured to exclude particles larger than 225μ, and most preferably is configured to exclude particles larger than 125μ.

In accordance with the invention, a port filter assembly may be disposed within the second port for maintaining a sterile environment in the apparatus. The port filter assembly preferably provides a gas permeable seal. Further, the port filter assembly may comprise a fritted filter disposed within an O-ring, the O-ring surrounded by a retaining ring.

The invention further provides that the container, the vessel cap, the filter tube assembly, and the first tube are constructed from a material having prescribed properties for preventing a chemical reaction with the demineralization solution. For example, such material may be selected from the group consisting of Teflon, glass, and ceramic.

In another embodiment of the invention, the apparatus for demineralizing osteoinductive bone further comprises a second tube connecting the second port to a vessel coupled to the pump. An ion exchange media is disposed within the vessel for regenerating the demineralization solution removed from the container. The pump is preferably operated at a rate of about 0.25 to 4.0 liters per min., more preferably operated at a rate of about 0.5 to 2.0 liters per min., and most preferably operated at a rate of about 1.0 liter per min. The ion exchange media may comprise a strong cation exchange resin, a strong anion exchange resin, or a strong cation exchange resin and a strong anion exchange resin.

BRIEF DESCRIPTION OF THE FIGURES

The invention is further explained in the description which follows with reference to the figures and drawings, by way of non-limiting examples, various embodiments of the invention, with like reference legends representing similarly collected data throughout the several figures and drawings.

FIG. 3 illustrates a second embodiment of the inventive apparatus for demineralizing bone according to the inventive process.

DESCRIPTION OF THE PREFERRED EMBODIMENTS

Figure 1:
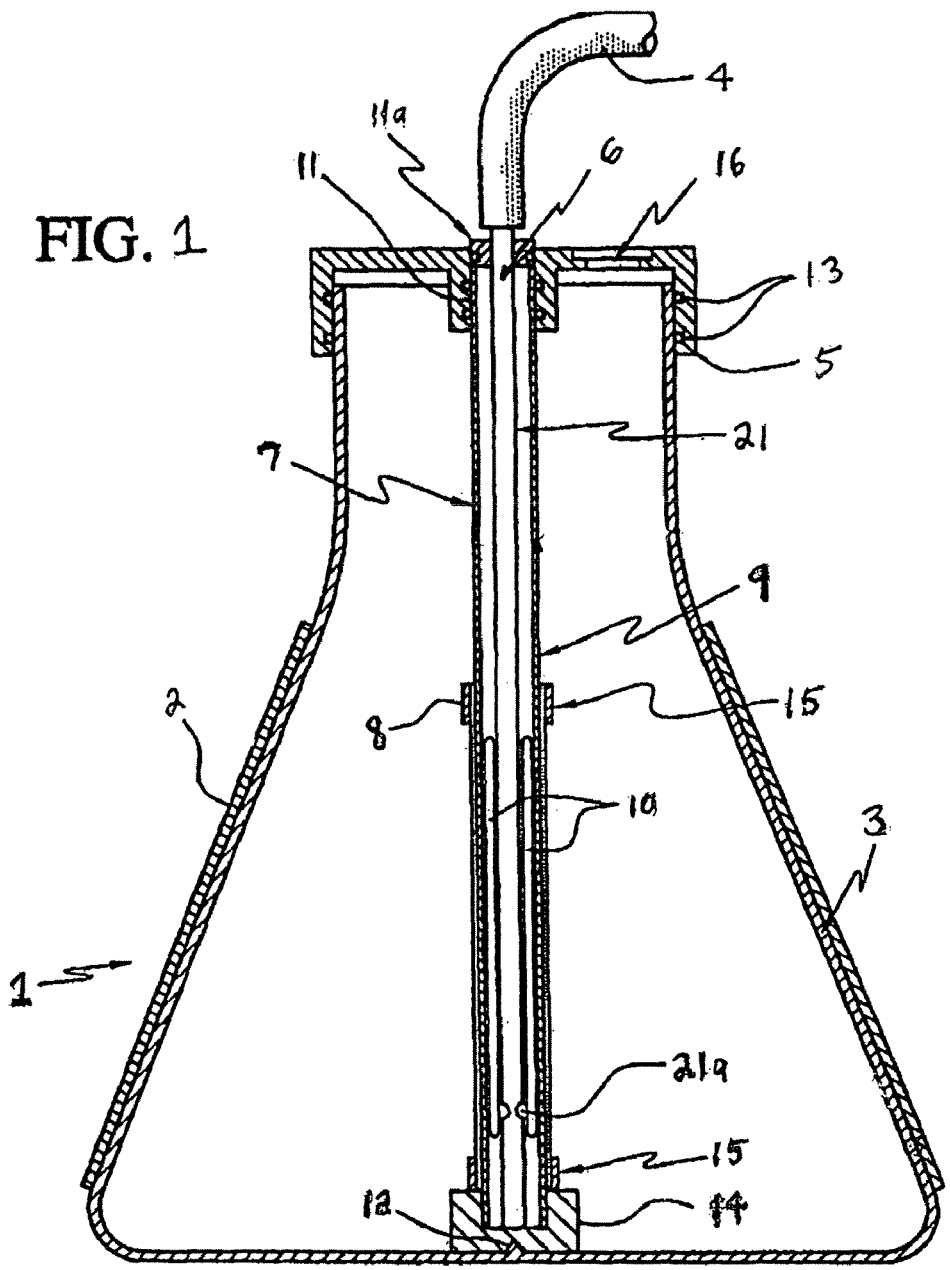
FIG. 1 illustrates a first embodiment of the inventive apparatus for demineralizing bone according to the inventive process.

I. Definitions:

The below definitions serve to provide a clear and consistent understanding of the specification and claims, including the scope to be given such terms.

Acid. By the term "acid" is intended any acid or solutions containing one or more acids, capable of demineralizing bone. For example, suitable acids include highly ionizable acids including, but not limited to, hydrochloric acid, and weakly ionizable acids including, but not limited to, citric acid. Suitable acids include, but are not limited to, organic acids such as formic acid, acetic acid, citric acid, or propionic acid; inorganic acids such as hydrochloric acid or phosphoric acid; physiological tissue-compatible hydroxy carboxylic acids including, but not limited to, citric acid, gluconic acid, malic acid, tartaric acid, fumaric acid, and phosphoric acid; combinations of acids which chelate (bind) calcium and/or amino carboxylic agents including chelators which chelate calcium including, for example, ethylenediaminetetraacetic acid (EDTA) (or analogues thereof), nitriloacetic acid (NTA), citric acid, succinic acid, and heparin. It has been found that these calcium chelating agent compositions, which bind calcium, aid in the demineralization of bone by both organic and inorganic acids. Such acid solutions may also include solutions of one or more acids in one or more alcohols. Any alcohol suitable for demineralizing bone such as, for example, ethanol and isopropyl alcohol (IPA). Other suitable acid solutions may include solutions of one or more acids in glycerol or other organic and/or inorganic metal remover, such as a metal chelator. Hydroxy carboxylic acids alone or in combination with amino carboxylic agents are advantageous for use in the demineralization process because they reduce the hydrolytic attack on bone morphogenic proteins present in the bone and because they are antioxidants, which serve as preservatives of the bone, thus eliminating the need for freeze drying the bone to preserve it.

Allowash™ Solution. By the term "Allowash™ solution" is intended for the purposes of this invention to include, for example, those detergent compositions disclosed in U.S. Pat. No. 5,977,034, incorporated herein by reference. Examples of suitable Allowash™ compositions include a cleaning composition containing about 0.06 wt % polyoxyethylene-4-lauryl ether; about 0.02 wt % poly (ethylene glycol)-p-nonyl-phenyl-ether; about 0.02 wt % octylphenol-ethyleneoxide and endotoxin free deionized/distilled water.

Bone. By the term "bone" is intended, for the purposes of the invention, any bone as one having ordinary skill in the art would envision. For example, the bone includes autograft bone, allograft bone and xenograft bone. Moreover, such bone includes any bone from any source, including, for example, human bone and animal bone. The bone may be from a living donor or a cadaveric donor. The bone may include cortical bone and/or cancellous bone and/or cortical cancellous bone and may be present in any form including, for example, ground bone, particulate bone (i.e. dental bone), bone chips, bone strips, bone cubes, bone fibers, and essentially intact bone. The bone may be in any size. For example, the particulate bone can be in any particle size range, such as, for example, from about 120µ to about 864µ.

Bone Marrow Elements. By the term "bone marrow elements" is intended the highly cellular hematopoietic connective tissue filling the medullary cavities and spongy epiphyses of bones which may harbor bacterial and/or viral particles and/or fungal particles, and includes, for example, blood and lipid.

Cycle. By the term "cycle" is intended one complete rotation of the tray of an orbital shaker, including, for example, orbital shaker by Troemner, Inc., Model 980001, Serial No: 1035, 500 watts. This orbital shaker is preferably operated at a setting of from about 150 to about 210 cycles/min., more preferably from about 160 to about 170 cycles/min., which settings correlate to about from 20 to about 60 cycles/min.

Detergent. By the term "detergent" is intended any agent which acts through a surface action, which possesses both hydrophilic and hydrophobic properties and/or exerts oil-dissolving (cleansing) and/or antibacterial and/or antiviral effects. Suitable detergents include, but are not limited to, anionic detergents, cationic detergents, acridine derivatives, long-chain aliphatic bases or acids, and Allowash™ detergent solutions.

Disinfectant. By the term "disinfectant" is intended one or more decontaminating agents which remove or inactivate/destroy any infectious material potentially present in the bone marrow of a bone graft. For example, potentially infectious material may include bacteria, virus and/or fungi. The disinfectant may include decontaminating agents such as, for example, an antibacterial agent; an antiviral agent; an antimycotic agent; an alcohol including, for example, methyl, ethyl, propyl, isopropyl, butyl, an/or t-butyl; trisodium phosphate; sodium hydroxide; hydrogen peroxide; and/or a detergent.

Drain. By the term "drain" is intended for the purposes of this invention, rapidly and substantially completely, draining or drawing off a volume of one or more demineralizing acids from a substantially closed processing container. Preferably, the demineralizing acid is substantially completely drained from the processing container in less than 10.0 minutes, more preferably in less than 9.0 minutes.

Lipid. By the term "lipid" is intended the fat-soluble constituents of bone marrow, including, for example, fatty acids, glycerides, and phospholipids.

Pulse. By the term "pulse" is intended for the purposes of this invention, rapidly and substantially completely, filling a substantially closed processing container with a predetermined volume of one or more demineralizing acids or acid solutions. Preferably, the container is substantially completely filled with the predetermined volume of demineralizing acid in less than 3.0 minutes, more preferably in less than 2.0 minutes.

Solvent. By the term "solvent" is intended for the purposes of the invention, a liquid cleaning composition capable of facilitating the solubilization of lipid, facilitating bone marrow removal, inactivating viral and/or bacterial particles, and/or disrupting cell membranes, and/or demineralizing bone. The liquid cleaning composition may contain one or more of the following: water; saline; a detergent; a disinfectant; an acid; an alcohol, for example, ethanol and/or isopropanol; solvents; a combination of solutes desired to facilitate solubilization of bone marrow, including, for example, Allowash™ detergent solutions; a chelating agent; a bactericidal agent; an antimycotic agent; sodium hydroxide or similar strong base; organic and/or inorganic acid known and used in the art for the demineralization of bone including, for example, hydrochloric acid; and/or hydrogen peroxide. Known lipophilic solvents include, for example, ethanol and chloroform.

Substantially Closed Processing Container. By the term "substantially closed processing container" is intended for the purposes of the present invention, any rigid or deformable container or reservoir of a size sufficient to contain bone and a predetermined volume of one or more demineralizing acids, composed of a material that is stable when in contact with the demineralizing acids, and is configured to allow the continuous exchange or pulsed exchange of acid.

Undesirable Constituents. By the term "undesirable constituents" is intended for the purposes of the present invention any constituents normally associated with a particular tissue whose presence in that tissue to be transplanted is undesirable. Non-limiting examples include, for example, blood cells, bacteria, fungi, and viruses. In the case of bone, bone marrow elements including lipid and blood, and any other constituents normally associated with bone marrow as well as any bacterial, viral or fungal contamination associated with the bone and/or bone marrow elements.

Ion Exchange Media. By the term "ion exchange media" is intended any media capable of removing calcium and/or from a demineralizing acid solution, including, for example, 8% cross-linked DOWER 50WX8 50-100 mesh, which is a cation exchange resin. Anion and cation resins are available with mesh sizes including 50-100, 100-200, and 200-400. There are three resin types, strong acid cation exchange resins designated as 50W, Type I strong base anion exchange resins designated as 1, and Type II strong base anion resins designated as 2. DOWER resins are fine mesh resins (Dow Chemical Co., Midlant, Mich.) and microporous copolymers of styrene and divinylbenzene (DVB). Cross-linkage is measured by percent DVB content, and includes 2, 4, and 8. As one skilled in the art would appreciate, this enables selection of optimum levels of permeability, water retention capacity, and total capacity. Suitable ion exchange media include mixtures of cation and anion resins and include, for example, one-third DOWER 50WX8 50-100 mesh, one-third DOWER 1 50-100 mesh, and one-third DOWER 2 50-100 mesh; one-half DOWER 1 50-100 mesh, C1 form and one-half DOWER 50WX8 50-100 mesh, H form; and 200-400 mesh at 1 liter per minute. However, is appreciated that one skilled in the art would be capable of selecting a suitable ion exchange resin to process bone.

Filter Mesh. By the term "filter mesh" is intended for the purposes of the invention any mesh composed of a material stable in the presence of the demineralizing solution having a mesh size sufficiently small so as to exclude bone particles. One skilled in the art is capable of selecting a suitable filter mesh in accordance with the present invention. Suitable filter mesh includes polyester monofilament having a mesh size of from 100µ to about 300µ, preferably from about 100µ to about 225µ, and most preferably about 125µ. Such filter mesh includes Pes125, (Industrial Fabrics Corp., Minneapolis, Minn.), which is a polyester monofilament mesh having a mesh size of 125µ.

The inventive process allows for the decalcification of an entire single donor's tissue volume in a single vessel over a tissue weight range of 100 to 800 grams or more at a rapid demineralization rate over a short period of time. The bone produced according to this invention is uniformly demineralized and optimally osteoinductive.

II. Procurement and Processing of Bone

Bone is procured and processed according to methods well known in the art to which the invention pertains. For example, bone is procured from a cadaver donor, cleaned of soft tissue, and bone marrow elements and undesirable constituents are removed. The bone is then processed to a desired form including, for example, ground into particulate bone, cut into cubes or strips, or left essentially intact. Bone is procured and processed under conditions according to accepted industry standards. Both cortical and/or cancellous bone is suitable for use in the inventive process.

III. Demineralization of Bone

Using the inventive process, bone is demineralized with acid at a concentration sufficient to demineralize bone. For example, relatively strong acids such as hydrochloric acid may be used at a concentration of from about 0.1N to about 3.0N. Relatively weak acids including, for example, citric acid, may be used at a concentration of from about 0.5N to about 5.0N. The acid, for example, citric acid, may be dissolved in one or more lipid soluble alcohols containing permeation enhancement surfactants to enhance the chemical reactivity and physical penetration of the acid into the mineral apatite of the bone. Weak acids including citric acid may be used in combination with low concentrations of strong acids including, for example, hydrochloric acid, to provide a demineralization system in which a desired pH, for example, a pH of about 1.2 has been found to correlate to and not exceed a residual calcium level of about 2.0 wt %, thus eliminating the potential of over-decalcifying the bone matrix.

The rate of demineralization, i.e., grams of bone demineralized per minute, can be increased or decreased as desired, by one of ordinary skill in the art to which the present invention pertains and without undue experimentation. As will be appreciated by an ordinary artisan, the rate of demineralization may vary based on factors which include: the reaction temperature; the concentration or normality of the acid and the acid's neutralization potential (strong or weak) in reacting with $Ca^{+2}$ hydroxy apatite; the acid's dissociation or percent ionization; the delivery rate of the acid to the bone or the bone to the acid; the mass, volume and density of the bone to be demineralized; the concentration of the calcium hydroxyapatite in the bone; the degree to which the bone has been cleaned of fat and protein; the surface area of the bone particles and their particle size distribution; the compaction of the bone upon contact with the acid by the action of the acid on the bone and the rate at which the products (calcium and phosphate) are removed from the acid; the method of agitation, i.e., mechanical stirring, shaking, orbital shaking, sonication, as well as other methods of agitation which provide uniform concentration of the reacting species and reduction of boundary layer resistance; and the degree to which a boundary layer resistance forms on the microporous surface of the bone particle and the packing of these particles with each other. Accordingly, the demineralization rate can be increased, for example, by increasing any one or more of the foregoing factors, for example, by increasing the temperature, acid concentration, surface area of the bone to be demineralized, or agitation. Likewise, the demineralization rate can be decreased by decreasing any one or more of the foregoing factors, for example, decreasing the acid concentration, slowing the delivery of acid, and/or increasing bone particle size.

In accordance with the present invention, the demineralizing acid solution may be pulsed into the ion exchange column containing the bone or continually pumped through an ion exchange column which removes both the cations (calcium) and anions (phosphate). In the event of the pulsed exchange, calcium is removed and the acid is drained. In the event of the continuous exchange, calcium is removed and the acid is continuously regenerated. Suitable ion exchange media includes an 8% cross-linked DOWER 50WX8 50-100 mesh, which will remove any calcium ions from dilute acid. The acid in the demineralizing acid solution competes with the calcium for the binding sites. While any concentration suitable to demineralize bone may be used, it has been found that the lower the concentration of acid, the greater the efficacy of calcium removal. Phosphate anion removal requires an anion exchange resin including, for example, DOWER 1 and DOWER 2. These ion exchange media will maintain the pH of the bone-acid reaction mixture thus eliminating the necessity of stopping the demineralization process in order to remove the solubilized calcium from the bone tissue. The ion exchange columns can be inactivated, for example, by a flow valve when it is time to wash the demineralized bone at the end of the demineralization process. The ion exchange columns can be reused, re-sterilized and through the use of "selectivity charts" can be optimized for efficacy.

The rapid demineralization inventive process is stopped when a desired residual calcium level of calcium in the bone matrix being demineralized has been reached. U.S. Pat. Nos. 6,189,537 and 6,305,379 are directed to methods for producing osteoinductive bone and the osteoinductive bone produced thereby, and are hereby incorporated herein by reference in their entirety. To determine a stopping point, a particular pH of eluent acid (exiting the reaction chamber prior to being run through an ion exchange media during recirculation), which correlates with the desired residual calcium level, must be determined. This is done by first obtaining a bone sample and determining the initial calcium concentration of the bone according to methods well known in the art to which the invention applies; demineralizing bone at a constant rate; simultaneous with demineralizing, periodically sampling the eluent acid solution and the bone from the closed reaction container at specific intervals of time during the demineralization process; determining the pH of each sample of acid solution and determining the residual calcium level of each corresponding bone sample; plotting the pH of a sample versus the calcium concentration of the corresponding bone sample, and drawing a curve; and from the curve determining what pH of the acid correlates with the desired residual calcium level. Thereafter, the residual calcium level of a bone sample can be determined by determining the pH of a sample of the acid solution, sampled at a time point during demineralization of the bone sample, by determining the calcium concentration on the curve which corresponds to the pH of the acid sample.

The amount of acid needed is that sufficient to demineralize bone to a desired residual level and may be determined according to known methods. In a preferred embodiment, the weight of the ground bone is first determined, the donor weight in grams is divided by 100 grams, and the resultant number is either multiplied by 3 liters for pulsed acid demineralization or multiplied by one liter for continuous acid demineralization. This is the total volume of acid needed to demineralize the given amount of ground bone. Other acids and desired calcium levels can be used by monitoring the calcium levels during demineralization at specific time points and plotting a curve to determine how much acid is used to reach a specific calcium level.

In the event of pulsed acid demineralization, the number of pulse/drain cycles needed may be calculated according to known methods. The total volume of acid needed to demineralize the given amount of bone is calculated and then divided by 4. This number is the number of pulse/drain cycles needed. Each pulse/drain cycle is carried out with 4 liters of acid.

For example, if the amount of ground bone is 425 grams, this number is divided by 100 grams to equal 4.25, which is then multiplied by 3 liters to yield a total acid volume of 12.75 liters. This number is then divided by 4 to yield 3.19 pulse/drain cycles. Thus, for 425 grams of bone, 12.75 liters of acid is needed, and processing includes 3 pulse/drain cycles using 4 liters each, and a fourth pulse/drain cycle using 0.75 liters of acid (the remainder).

In this calculation, there must be at least two pulse/drain cycles, and each cycle must include at least 5.0 min. incubation. This calculation is specific for 0.5N HCl and for reaching 2% residual calcium.

IV. Apparatus for Demineralizing Bone

FIG. 1 illustrates the apparatus 1 of the invention for pulsed acid demineralization of bone. Bone is demineralized by placing bone, for example, ground bone, in container 3 holding a demineralization solution, for example, one or more acids at a concentration sufficient to demineralize bone, and in a volume sufficient to process the amount of bone to be demineralized, for example, from about 2.0 to about 8.0 liters, preferably from about 3.0 to about 6.0 liters of acid. The container 3 optionally includes heating blanket or thermal wrap 2.

Thereafter, a defoaming agent is added to the container through tubing 4 connected to a first port 6 on the vessel cap 5. Vessel cap 5 is connected to container 3 via O-rings 13. The defoamer flows into container 3 through filter tube assembly 7 disposed within the first port 6. Filter tube assembly 7 includes the filter mesh 8 disposed over the filter tube 9 optionally having openings 10, and a downtube 21 optionally having openings 21a (at least two). The filter tube assembly 7 is connected at its top end to a vessel cap 5 via a connection 11 and top end cap 11a. This connection can be a threaded connection, a frictional connection, a connection via O-rings, or the equivalent. The filter tube assembly 7 is connected at its bottom end to end cap 14 via, for example, a press fit, a frictional fit, a threaded connection, or via O-rings or the equivalent. The filter tube assembly 7 at its bottom end may be seated on protrusion 12 of container 3. The keeper rings 15 may be used to anchor filter mesh 8 to filter tube 9.

The filter mesh 8 may be composed of any material stable in the presence of the demineralizing solution, such as polyester or Teflon, or an equivalent material. The filter mesh may be any size suitable to exclude bone particles. In a preferred embodiment, the mesh size is about 125μ.

Suitable defoamers include any defoamers well known in the art to which the invention pertains, and include, for example, ethanol. Any amount of ethanol suitable for defoaming, such as 60 mls of 200 proof ethanol in 6.0 liters of acid, may be used. The bone-acid-ethanol solution is then preferably vigorously agitated by known methods. For example, the closed apparatus may be exposed to orbital shaking at a rate sufficient to keep the bone particles in suspension, for example, at from about 20 to about 60 cycles per minute on an orbital shaker table, while the system is maintained at a desired temperature, for example, of from about 15° C. to about 100° C., preferably from about 15° C. to about 50° C., more preferably from about 20° C. to about 40° C., and most preferably at about 23° C.

After an initial period of time, for example, five minutes, substantially all, for example 90% to 95%, of the acid is then rapidly drained from container 3 through tubing 4 connected to the first port 6 on vessel cap 5, via a vacuum pump connected to tubing 4. The acid solution is thus rapidly pulled through the first port 6, through filter mesh 8 covering filter tube 9 of filter assembly 7, and downtube 21 having openings 21a, and exiting the container 3 via tubing 4. Container 3 was then refilled with the demineralizing solution, via tubing 4 connected to the first port 6 on vessel cap 5, and flowing into container 3 through downtube 21 and filter mesh 8 covering filter tube 9 of filter assembly 7. The contents of the container 3 were again agitated for a second period of time, for example, about ten minutes. The container 3 was optionally again rapidly drained, refilled, and agitated for a third period of time, for example, 20 minutes.

Figure 2:
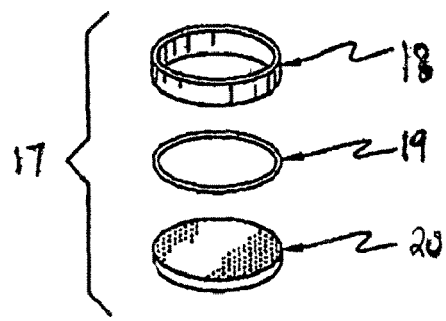
FIG. 2 illustrates a side view of the inlet port filter assembly.

The acid was then drained and a buffer solution was added to container 3 through tubing 4 connected to vessel cap 5 and filter assembly 7, to stop the demineralizing reaction. Vessel cap 5 further includes a second port 16 used to fill the reaction vessel 2 with bone. Thereafter, port filter assembly 17, illustrated in FIG. 2, including retaining ring 18, O-ring 19, and fritted filter 20, is placed in the port to allow maintenance of the closed system during pulse and drain exchanges. Gas can sterilely leave or enter container 3 via port filter assembly 17. All of the components of apparatus 1 can be composed of any material stable in the presence of the demineralizing solution. Suitable materials include Teflon, glass, and ceramic.

FIG. 3 illustrates the apparatus 22 of the invention for continuous acid demineralization of bone. Bone is demineralized by placing bone, for example, ground bone, in reaction vessel 23 containing a demineralization solution, for example, one or more acids at a concentration sufficient to demineralize bone, and in a volume sufficient to process the amount of bone to be demineralized, for example, from about 2.0 to about 10.0 liters, preferably from about 3.0 to about 7.0 liters of acid.

Thereafter, a defoaming agent is added to the vessel 23 through inflow tubing 27 connected to inlet port 26. Suitable defoamers include any defoamers well known in the art to which the invention pertains, and include, for example, ethanol. Any amount of ethanol suitable for defoaming, such as 60 mls of 200 proof ethanol in 6.0 liters of acid, may be used. The bone-acid-ethanol solution is then preferably vigorously agitated by known methods. The closed apparatus may be stirred at from about 500 rpm to about 2500 rpm, preferably 1000 rpm to about 2000 rpm, and more preferably stirred at about 1350 rpm with mixing paddle 28, for example Cole Palmer Model No: E-04541-00 303/304 supplied by Cole Palmer Instrument Co., Vernon Hills, Ill. The closed apparatus 22 may also be agitated by orbital shaking while the system is maintained at a desired temperature, for example, of from about 0° C. to about 100° C., preferably from about 15° C. to about 50° C., more preferably from about 20° C. to about 40° C., and most preferably at about 23° C.

The demineralizing acid solution is continuously exchanged by pumping the acid solution from the reaction vessel 23, through outlet port 24, through outflow tubing 25, which tubing runs through pump 28. Pump 28 is operated at from 0.25 to 4.0 liters per min., preferably 0.5 to 2.0 liters per min, and most preferably about 1.0 liter per min. The eluent acid solution is delivered to ion exchange media vessel 29 through inlet 30. As the acid solution is continually pumped and calcium and phosphate are removed from the acid solution by the ion exchange media 32, the regenerated acid exits the ion exchange media at outlet 31 and flows back into the reaction vessel 23 through inflow tubing 27. The ion exchange media vessel 29 is disposed on a magnetic stir plate to stir the ion exchange media 32 during the process. The reaction vessel 23 is disposed on an orbital shaker to agitate the acid/bone mixture during processing.

All of the publications cited herein are hereby incorporated by reference into the present disclosure. It will be appreciated by those skilled in the art to which the invention pertains that various modifications can be made without departing from the essential nature thereof. It is intended to encompass all such modification within the scope of the appended claims.

We claim:

1. An apparatus for demineralizing osteoinductive bone, consisting of:
   a container for holding demineralization solution and the osteoinductive bone;
   a vessel cap covering said container, said vessel cap containing a first port, and a second port for introducing the osteoinductive bone into said container;
   a filter tube assembly disposed within said first port for transporting said demineralization solution into and out of said container,
   said filter tube assembly being configured to exclude particles larger than a prescribed size; a pump for removing said demineralization solution from said container, and
   a first tube connecting said first port to said pump.

2. The apparatus of claim 1, wherein said filter tube assembly contains a plurality of openings along a predetermined portion thereof.

3. An apparatus for demineralizing osteoinductive bone, consisting of:
   a container for holding demineralization solution and the osteoinductive bone;
   a vessel cap covering said container, said vessel cap containing a first port, and a second port for introducing the osteoinductive bone into said container;
   a filter tube assembly disposed within said first port for transporting said demineralization solution into and out of said container,
   said filter tube assembly being configured to exclude particles larger than a prescribed size; a pump for removing said demineralization solution from said container,
   a first tube connecting said first port to said pump, and
   a port filter assembly disposed within said second port for maintaining a sterile environment in said apparatus.

4. The apparatus of claim 3, wherein said port filter assembly provides a gas permeable seal.

5. The apparatus of claim 1, wherein said filter tube assembly is configured to exclude particles larger than 300μ.

6. The apparatus of claim 1, wherein said filter tube assembly is configured to exclude particles larger than 225μ.

7. The apparatus of claim 1, wherein said filter tube assembly is configured to exclude particles larger than 125μ.

8. The apparatus of claim 1, wherein said container, said vessel cap, said filter tube assembly, and said first tube are constructed from a material having prescribed properties for preventing a chemical reaction with said demineralization solution.

9. The apparatus of claim 8, wherein said material is selected from the group consisting of Teflon, glass, and ceramic.

10. An apparatus for demineralizing osteoinductive bone, consisting of:
    a container for holding demineralization solution and the osteoinductive bone;
    a vessel cap covering said container, said vessel cap containing a first port, and a second port for introducing the osteoinductive bone into said container;
    a filter tube assembly disposed within said first port for transporting said demineralization solution into and out of said container,
    said filter tube assembly being configured to exclude particles larger than a prescribed size; a pump for removing said demineralization solution from said container,
    a first tube connecting said first port to said pump, and
    a second tube connecting said second port to a vessel coupled to said pump.

11. An apparatus for demineralizing osteoinductive bone, consisting of:
    a container for holding demineralization solution and the osteoinductive bone;
    a vessel cap covering said container, said vessel cap containing a first port, and a second port for introducing the osteoinductive bone into said container;
    a filter tube assembly disposed within said first port for transporting said demineralization solution into and out of said container, said filter tube assembly being configured to exclude particles larger than a prescribed size;
    a pump for removing said demineralization solution from said container;
    a first tube connecting said first port to said pump;
    a second tube connecting said second port to a vessel coupled to said pump;
    wherein an ion exchange media is disposed within said vessel for regenerating said demineralization solution removed from said container.

12. The apparatus of claim 10, wherein said pump is operated at a rate of about 0.25 to 4.0 liters per min.

13. The apparatus of claim 10, wherein said pump is operated at a rate of about 0.5 to 2.0 liters per min.

14. The apparatus of claim 10, wherein said pump is operated at a rate of about 1.0 liter per min.

15. The apparatus of claim 11, wherein said ion exchange media comprises a strong cation exchange resin.

16. The apparatus of claim 11, wherein said ion exchange media comprises a strong anion exchange resin.

17. The apparatus of claim 11, wherein said ion exchange media comprises a strong cation exchange resin and a strong anion exchange resin.

18. An apparatus for demineralizing osteoinductive bone, consisting of:
a container for holding demineralization solution and the osteoinductive bone;
a vessel cap covering said container, said vessel cap containing a first port, and a second port for introducing the osteoinductive bone into said container;
a filter tube assembly disposed within said first port for transporting said demineralization solution into and out of said container, said filter tube assembly being configured to exclude particles larger than 125µ, and said filter containing a plurality of openings along a predetermined portion thereof;
a pump for removing said demineralization solution from said container; and
a first tube connecting said first port to said pump.

19. An apparatus for demineralizing osteoinductive bone, consisting of:
a container for holding demineralization solution and the osteoinductive bone;
a vessel cap covering said container, said vessel cap containing a first port, and a second port for introducing the osteoinductive bone into said container;
a filter tube assembly disposed within said first port for transporting said demineralization solution into and out of said container, said filter tube assembly being configured to exclude particles larger than a prescribed size;
a pump for removing said demineralization solution from said container;
a first tube connecting said first port to said pump; and a second tube connecting said second port to a vessel coupled to said pump, wherein an ion exchange media is disposed within said vessel for regenerating said demineralization solution removed from said container.

20. An apparatus for demineralizing osteoinductive bone, consisting of:
a container for holding demineralization solution and the osteoinductive bone;
a vessel cap covering said container, said vessel cap containing a first port, and a second port for introducing the osteoinductive bone into said container;
a filter tube assembly disposed within said first port for transporting said demineralization solution into and out of said container, said filter tube assembly being configured to exclude particles larger than 125µ, and said filter containing a plurality of openings along a predetermined portion thereof;
a pump for removing said demineralization solution from said container; a first tube connecting said first port to said pump; and
a second tube connecting said second port to a vessel coupled to said pump, wherein an ion exchange media is disposed within said vessel for regenerating said demineralization solution removed from said container.

* * * * *